US009316748B2

(12) United States Patent
Mapelli et al.

(10) Patent No.: US 9,316,748 B2
(45) Date of Patent: Apr. 19, 2016

(54) MICROFABRICATED SCINTILLATION DETECTOR

(75) Inventors: Alessandro Mapelli, Ferney-Voltaire (FR); Pietro Maoddi, Chavanne-Pres-Renes (CH); Philippe Renaud, Preverenges (CH)

(73) Assignee: CERN—European Organization for Nuclear Research, Geneva (CH)

( * ) Notice: Subject to any disclaimer, the term of this patent is extended or adjusted under 35 U.S.C. 154(b) by 0 days.

(21) Appl. No.: 14/399,907

(22) PCT Filed: May 8, 2012

(86) PCT No.: PCT/EP2012/001980
§ 371 (c)(1),
(2), (4) Date: Nov. 7, 2014

(87) PCT Pub. No.: WO2013/167151
PCT Pub. Date: Nov. 14, 2013

(65) Prior Publication Data
US 2015/0105603 A1 Apr. 16, 2015

(51) Int. Cl.
*G01T 1/20* (2006.01)
*G01T 5/08* (2006.01)
(Continued)

(52) U.S. Cl.
CPC ............ *G01T 1/2006* (2013.01); *A61N 5/1048* (2013.01); *G01T 1/201* (2013.01); *G01T 1/29* (2013.01); *G01T 5/08* (2013.01); *Y10T 29/49002* (2015.01)

(58) Field of Classification Search
CPC ........... G01T 1/2018; G01T 1/20; G01T 1/24; H01L 27/14663; H04N 5/32; G01N 21/03; G01N 21/05
See application file for complete search history.

(56) References Cited

U.S. PATENT DOCUMENTS

| 4,942,302 A | * | 7/1990 | Koechner | ................ G01T 1/203 250/366 |
| 2010/0032578 A1 | * | 2/2010 | Levene | ................. G01T 1/1644 250/370.11 |

OTHER PUBLICATIONS

Mapelli et al. "Development and studies of a novel microfabricated radiation hard scintillation particle detector with high spatial resolution", Nuclear Physics B. Proceedings Supplement, North-Holland, Amsterdam, NL, vol. 197, No. 1, Dec. 15, 2009, pp. 43-47, XP026917670.*

(Continued)

*Primary Examiner* — David Porta
*Assistant Examiner* — Mamadou Faye
(74) *Attorney, Agent, or Firm* — Marshall, Gerstein & Borun LLP

(57) ABSTRACT

The present invention discloses a microfabricated scintillation detector, comprising a channel structure (26) for containing a liquid scintillator material therein and flowing said liquid scintillator material therethrough. The channel structure (26) comprises first and second sets (30, 36) of adjacent channel portions (32, 38) arranged in first and second layers (34, 40) and in fluid communication with each other. The second set (36) of adjacent channel portions (38) is directed at right angles with respect to the first set (30) of adjacent channel portions (32). The first and second layers (34, 40) are stacked on top of each other with a separation layer (42) in between, integrally connecting said first and second layers (34, 40). The channel structure (26) simultaneously forms a light guiding structure for guiding scintillation light (52) towards a longitudinal end of the corresponding channel portion (32, 38). The scintillation detector (24) further comprises a plurality of photo detectors (54), arranged such as to receive said scintillation light (50).

26 Claims, 9 Drawing Sheets

(51) Int. Cl.
*A61N 5/10* (2006.01)
*G01T 1/29* (2006.01)

(56) References Cited

OTHER PUBLICATIONS

Haguenauer et al. "microfluidic scintillating detector (proof of principle)" 11th Topical Seminaron Innovative Particle and Radiation Detectors (IPRD08), Oct. 1-4, 2008, Siena, Italy.*

Mapelli et al., "Development and studies of a novel microfabricated radiation hard scintillation particle detector with high spatial resolution," Nuclear Physics B. Proceedings Supplement, 197(1):43-47.

Haguenauer et al., "Microfluidic scintillating detector (proof of principle)", https://twili.cern.ch/twiki/pub/marin/alessandromapelli/mapelli_sienna08_sub_talk.pdf, pp. 6-21 (2013).

* cited by examiner

MICROFABRICATED SCINTILLATION DETECTOR

The present invention relates to particle and radiation detectors. In particular, the present invention relates to a microfabricated scintillation detector comprising a liquid scintillator material.

FIELD OF THE INVENTION

Scintillation detectors for detecting ionizing radiation have been known since the 1940s. A scintillator is a material capable of emitting photons in the visible or UV spectrum when being passed by charged particles. In a scintillation detector, radiation is indirectly detected by detecting the scintillation light generated by the radiation in the scintillating material by means of a suitable photodetector.

FIG. 1 is a perspective exploded view of a typical prior art scintillation detector 10. As seen in FIG. 1, the scintillation detector comprises a collimator grid 12 consisting of a metallic or other high-Z material structure that filters out, i.e. absorbs incoming radiation with oblique angles with regard to the detector plane. The purpose of the collimator grid is to reduce noise and cross-talk between pixels, thereby increasing the image resolution.

Below the collimator grid 12, a scintillating material layer 14 is provided. In the example of FIG. 1, the scintillating material layer 14 is structured in separate pillars 16 that act as light traps or waveguides so that cross-talk between pixels is reduced. Note that the light is guided through the pillars 16 in a direction parallel with respect to the incident radiation, i.e. in a perpendicular or out-of-plane direction with respect to the detector plane. Below the scintillating material layer 14, a photodetector matrix layer 18 is provided.

Reference sign 20 designates a trajectory of a particle passing the collimator grid 12 and one of the pillars 16 of the scintillating material layer 14. Upon interaction with the scintillating material pillar 16, a scintillation flash 22 is generated in the pillar 16 that can be detected by a corresponding photodetector or group of photodetectors associated with the scintillating pillar 16.

The scintillation detector design as shown in FIG. 1 has proven to be very successful in X-ray imaging as well as for detecting high energy particles. In particular, the spatial resolution of the detector design as shown in FIG. 1 is very high. However, the scintillation detector design of FIG. 1 also has drawbacks in practice. One of the drawbacks of the design of FIG. 1 is the comparatively low radiation resistance. Since the photo detector array 18 is arranged in the detector plane, the photo detectors are constantly exposed to the radiation field to be detected, which, depending on the radiation field intensity, leads to an increased aging of the photo detectors. The same is also true for the scintillating material layer 14, which may also be worn out by radiation.

Further, the scintillation detector 10 of FIG. 1 has a comparatively high material budget, meaning that it employs comparatively much material more to be passed by the incident radiation with a correspondingly high absorption. Accordingly, the detector 10 of FIG. 1 is less suitable for e.g. monitoring a radiation beam, since due to its high material budget it will significantly perturb the radiation beam when passing therethrough.

Alternative radiation detectors with lower material budget are so-called wire chambers. The drawback of wire chambers, however, is that they saturate at high radiation fluxes and that they require permanent maintenance and gas supply. This makes them difficult for use outside a laboratory environment, such as in medical devices.

Another class of scintillation detectors is based on scintillating fibers. However, when arranging scintillating fibers in multiple planes such as to achieve a high spatial resolution, a high material budget is again obtained.

A further scintillation type detector is based on glass capillaries filled with liquid scintillators. The advantage of using liquid scintillator material is that it can be readily replaced, thereby making the scintillator intrinsically "radiation hard". While good results in terms of particle track reconstruction have been found with liquid scintillator filled glass capillaries, the manufacture turns out to be quite demanding, in particular with regard to drawing, assembling, cutting and filling the capillary bundles.

The inventor has earlier developed a scintillation detector comprising a dense area of scintillating waveguides obtained by filling microfluidic channels with an organic liquid scintillator, see *Development and Studies of a Novel Microfabricated Radiation Hard Scintillation Particle Detector with High Spatial Resolution*, A. Mapelli et al., *Nuclear Physics B (Poc. Suppl.)* 179 (2009), 43-47. In this detector, a plurality of parallel micro channels are provided in an SU-8 resin formed on top of a silicon substrate wherein the silicon substrate provides structural support. The channels are closed with foils of Al-coated Mylar. The micro channel design defines 50 μm wide waveguides arranged in a serpentine geometry and separated by 10 μm wide SU-8 walls, and the channel walls and bottom are coated with a 200 nm reflective gold layer making the micro channels act as optical waveguides. The 60 μm pitch of the channel fans out to a pitch of 2.3 mm to match the inter-pixel distance of a multi-anode photomultiplier tube.

Due to the silicon substrate and the Al-coated Mylar foil, the material budget of the detector was still comparatively high. However, providing the silicon substrate was believed to be required in order to provide structural support.

Further, this earlier detector proposed by the inventor was only capable of detecting in which of the channels scintillation light was generated, i.e. it essentially only allowed for a one-dimensional detection. While it would in principle be possible to stack two of these detectors on top of each other with the channels oriented at right angles, such as to obtain 2D detection, this would have doubled the material budget. Also, the two individual detectors would have to be arranged with respect to each other with great precision.

SUMMARY OF THE INVENTION

The object underlying the present invention is to provide a radiation hard scintillation detector that also has a comparatively low material budget.

This object is achieved by a microfabricated scintillation detector according to claim 1, as well as by a method of manufacturing such scintillation detector according to claim 21. Further advantageous developments are defined in the dependent claims.

In the present disclosure, the term "microfabrication" means fabrication processes as generally known from semiconductor manufacturing and may include one or more of deposition or growth of material on the substrate, patterning of material layers, etching, microcutting or micromilling.

The scintillation detector of the invention comprises a channel structure for containing a liquid scintillator material therein and flowing said liquid scintillator material therethrough. The channel structure comprises a first set of adjacent channel portions arranged in a first layer and in fluid communication with each other. The channel structure further comprises a second set of adjacent channel portions arranged in a second layer and in fluid communication with each other, said second set of adjacent channel portions being directed transversely, preferably at right angles, with respect to the first set of adjacent channel portions. The first and second layers are stacked on top of each other with a separation layer in between, said separation layer integrally connecting said first and second layers.

The channel structure simultaneously forms a light guiding structure for guiding scintillation light generated upon interaction of radiation with said liquid scintillator material in said adjacent channel portions towards a longitudinal end of the corresponding channel portion. Further, the scintillation detector comprises a plurality of photo detectors arranged such as to receive said scintillation light.

Herein, the channel portions in the first set of adjacent channel portions are preferably arranged in parallel in said first layer. Likewise, the channel portions in the second set of adjacent channel portions are preferably arranged in parallel in the second layer. Further, the second set of adjacent channel portions is preferably directed at right angles with respect to the first set of adjacent channel portions. However, it should be noted that the adjacent channel portions need not necessarily be parallel in order to provide a functional embodiment. In fact, in some embodiments of the invention described in more detail below, where the channel walls are employed as light guiding structures, non-parallel channel walls may be preferred.

Further, in some embodiments, the photodetectors may be arranged in proximity to the longitudinal ends of the adjacent channel portions such as to directly receive the scintillation light. However, in other embodiments it may be advantageous to dispose the photodetectors some distance away from the channel structure for practical purposes. In this case, light guiding means can be provided between a location in proximity of the longitudinal ends of the adjacent channel portion and the photodetectors, such as optical fibres or the like.

According to the invention, two sets of adjacent channel portions are employed which are directed transversely, in some embodiments at right angles with respect to each other. This way, a particle trajectory passing two channel portions in two different layers will cause scintillation light propagating towards the corresponding photo detectors in two linearly independent, e.g. orthogonal directions, thereby allowing to obtain two-dimensional information about the location where the particle trajectory crosses the scintillation detector.

Importantly, the first and second layers are integrally connected with each other by means of a separation layer which at the same time allows to cover the channels on the side facing the separation layer. As will be demonstrated in more detail below, using microfabrication technology, this separation layer can be made extremely thin, thereby minimizing the material budget of the detector in spite of employing at least two channel layers.

Note that in the one-layer device previously proposed by the inventor, a silicon substrate was necessary for providing structural support for the channel confining material. However, when integrally connecting the first and second layers by the separation layer, the first and second layers mutually provide structural support for each other, thereby alleviating the need for an additional substrate or the like. This way, the material budget of the two-layer device can be even considerably less than that of the previously proposed one layer device, with the additional benefit of allowing to provide intrinsically two-dimensional measurements.

In a preferred embodiment, the first and second sets of adjacent channel portions are in fluid communication with each other as well. This means that the same scintillation liquid can flow through both sets of adjacent channel portions, such that the entire two layer structure would only need a single fluid supply and fluid outlet for exchanging scintillator liquid or for circling scintillator liquid through the channel portions in both layers. This makes exchanging the scintillator liquid much more convenient than for example in the case of glass capillaries filled with liquid scintillators, where the filling actually turns out to be quite involved. In fact, according to this embodiment of the invention, it is even possible to continuously circulate scintillator material through the first and second sets of adjacent channel portions during radiation detection.

In a preferred embodiment, each of said first and second sets of adjacent channel portions are part of a corresponding serpentine-shaped channel, in which neighboring channel portions are alternately connected at one of their longitudinal ends. This way, the adjacent channel portions are arranged in a single, non-bifurcated conduit that proves to be ideal for flowing liquid therethrough.

Further, the serpentine channels formed in the first and second layers are preferably connected by a vertical channel portion extending through said separation layer such as to form a single channel running through said first and second layers.

As mentioned before, the separation layer separating the adjacent channel portions in said first and second layers can be comparatively thin, thereby decreasing the material budget of the detector as a whole. In particular, the thickness of the separation layer may be 150 µm or less, preferably 100 µm or less, more preferably 60 µm or less and most preferably 30 µm or less. In spite of this comparatively small thickness, the separation layer may serve to cover the channels of both adjacent layers and to integrally connect said first and second layers which thereby provide mutual structural support for each other, without need for any further stabilizing substrate.

Preferably, the width of said parallel channel portion is 500 µm or below, more preferably 300 µm or below. Note that the channel width corresponds to the intrinsic spatial resolution of the scintillation detector. Further, the height of the adjacent channel portions is preferably 1000µ or below, more preferably only 100 µm or below. Note again that a comparatively small channel height helps to decrease the material budget of the detector as a whole.

In a preferred embodiment, the ratio of channel width: channel height of the adjacent channel portions 32, 38 is ≥0.5, preferably ≥1.0 and most preferably ≥1.5.

In a preferred embodiment, the plurality of photo detectors is formed by an array of photo detectors having the same pitch as the corresponding channel portions in the first and second sets of adjacent channel portions. This way, the detector array can be disposed directly at the end sections of the adjacent channel portions, without any need to fan out the channel portions or the like.

Please note that the liquid scintillator filled channels resemble the only active part of the detector. Since channel sidewalls are needed to define the channel structure, which themselves are not active in detection, this means that the coverage provided by a single layer is necessarily less than 100%. In a preferred embodiment, the scintillation detector therefore further comprises a third and/or a fourth set of adjacent channel portions arranged in a third and fourth layer, respectively, wherein the channel portions in said third/fourth set of adjacent channel portions are arranged in parallel to and staggered with regard to the channel portions in said first/second set of adjacent channel portions. Herein, a "staggered arrangement" means that the channel portions are shifted with respect to each other in the detector plane such that the channels are not vertically aligned with each other. Instead, it would, for example, be advantageous that the channel portions of the third (fourth) layer are vertically aligned with the separation walls of the first (second) layer, or the like.

Needless to say, even more layers could possibly be provided. This would not only allow a coverage of 100%, but also a 3D-detection, although at the price of an increased material budget. Also, everything said about the first and second layers could similarly apply for the additional layers, including the serpentine structure, without explicit mention. Also, in a preferred embodiment, all the channels within all the layers would be in fluid communication, so that still the entire detector would only need a single inlet and outlet for flowing the liquid scintillator therethrough.

As mentioned before, the channel structure simultaneously forms a light guiding structure for guiding scintillation light generated upon interaction of radiation with said liquid scintillator material in said adjacent channel portions towards the longitudinal end of the corresponding channel portion. One way of achieving this would be to provide a reflective coating to the channel walls, in particular a metal coating, such as an aluminum or gold coating. This way, the channels themselves act as a light guide based on optical reflection at the metallic coating of the channel walls.

While such reflective coating allows for a comparatively small attenuation of the scintillation signal at short channel lengths, such metal coating may also have drawbacks, in particular with regard to the integrated two or more layer design of the present invention. Namely, when employing a metal coating to the channel walls, including a metal coating of the separation layer, this turns out to make the bond between the first and second layers and the separation layer more difficult to achieve. Also, the metallic coating may add to the perturbation of the radiation field. Finally, for long adjacent channel portion lengths, the attenuation of the scintillation signal becomes quite severe.

Accordingly, in an alternative embodiment, the channel walls defining the adjacent channel portions are made from or covered with a dielectric material having a refractive index in the emission spectrum of the liquid scintillator to be used in said scintillation detector that is lower than that of the liquid scintillator, in particular a refractive index of 1.47 or below, more preferably 1.35 or below, and most preferably 1.30 or below. Suitable materials are, for example, Pyrex glass, NOA 13685, NOA 1375, Perfluoroalkoxy or fluorinated (ethylenic-cyclooxyaliphatic substituted ethylenic) copolymer. Note that in the present disclosure, the expression "emission spectrum of the liquid scintillator" refers to the spectrum of the scintillator light that is actually detected at the detector and that needs to be guided along the adjacent channel portions.

This way, the channels may serve as light guides as well, however, not based on optical reflection from a metallic surface but based on total internal reflection at the liquid/solid interface, thereby circumventing the problems mentioned above with respective to metal coating.

Further, and quite surprisingly, it turns out that for longer light guiding distances, the transport of light guiding due to total internal reflection at the liquid/solid interface turns out to be even less attenuated than in case of optical reflection at a metal coating. This may be surprising at first sight indeed, because only an angular fraction of the scintillation light that obeys the condition of total internal reflection can be guided by the channel structure and hence contribute to the scintillation signal, while the remaining angular portion of the scintillation light is lost. However, the fraction of this scintillation light that does meet the total internal reflection condition can then be refracted internally many times at the liquid solid interface with only moderate further attenuation. In contrast to this, it is found that while a metallic coating will allow scintillation light of all incident angles to be reflected, the attenuation occurring for multiple reflections at the metal coated channel walls adds up considerably and thereby severely attenuates the signal.

Further, while according to the invention the channel structure forms a light guiding structure for guiding the scintillation light generally towards the longitudinal end of the corresponding channel portion, this is not meant to imply that the channels themselves act as the light guides. Instead, in an alternative embodiment, at least a part of the channel confining material exposed to the liquid scintillator when in operation may have an index of refraction that is higher than that of the liquid scintillator to be used in said microfabricated scintillation detector. This way, the scintillation light will not be confined in the channel by total internal reflection, since the scintillation light will actually enter the higher refraction index material instead. In this embodiment, the higher refractive index material is then acting as a light guide for capturing scintillation light and guiding the same to a corresponding photo detector.

For example, the channel confining material acting as a light guide may be formed by the sidewalls separating neighboring channel portions. In this embodiment, the photo detectors are associated with respective ones of said sidewalls such as to receive scintillation light guided through the respective sidewall. Further, the scintillation detector comprises a readout means suitable for detecting simultaneous light signals in adjacent sidewalls confining the same channel portion.

Namely, when the sidewalls have a higher index of refraction than the scintillator liquid, the scintillation light will tend to escape to both of the sidewalls confining the channel, and scintillation light will be simultaneously detected by the two photo detectors associated with the two channel sidewalls. From a single photo detector signal it could not be told yet in which of the channels the scintillation light was generated, because typically each sidewall will be exposed to two different channel portions. However, by detecting simultaneous light signals in adjacent sidewalls confining the same channel, the signal can clearly be attributed to this channel portion.

In yet a further embodiment, the channel confining material acting as a light guide can be formed by a rib-like structure provided on the bottom of the adjacent channel portions. This embodiment is advantageous with regard to avoiding crosstalk between signals.

In yet a further embodiment, the channel side walls may have outer portions that are exposed to the scintillator liquid when in operation and that have an index of refraction that is similar to or higher than that of the scintillator liquid to be used with said detectors, and an inner portion having an index of refraction that is lower than that of the scintillator liquids. Herein, the inner portion may in particular be a hollow portion. This embodiment is functionally very similar to an embodiment where the side walls themselves have a low refractive index, except that in this embodiment, the total internal reflection does not occur at the liquid solid interface but at the interface between the outer and inner portions of the channel side wall. The advantage of this embodiment is that the material forming the outer portions of the side wall can be chosen according to manufacturability considerations but does not need to have a low index of refraction itself. In contrast to this, if the total internal reflection is to occur at the liquid/side wall interface, one always has to find a compromise between manufacturability and low refractive index.

As mentioned before, the microfabricated scintillation detector of the invention combines an intrinsic radiation hardness with a low material budget. This makes it particularly useful for use as a beam profiler, in particular for use as a beam profiler for monitoring the radiation profile of a medical beam, such as a hadron beam. In view of the very low material budget of the detector of the invention, it becomes even possible to keep the beam profiler in the therapeutic hadron beam during patient radiation, thereby allowing online beam monitoring. To the knowledge of the inventor, this is not possible so far with any other radiation detector, and it is believed to be of tremendous practical value in hadron beam therapy, since it allows detection of instabilities in the beam during treatment and to carry out real time dosimetry to name but two advantages.

When used as a beam profiler, depending on the radiation flux it may be possible to detect "single events", i.e. scintillation flashes attributable to a single radiation quantum and to analyze the beam profile based on such single events. However, using suitable readout means for receiving signals from the photo detectors and analysis means, the beam profile information can even be calculated therefrom if single events are no longer distinguishable.

Further, the invention provides a method of manufacturing a scintillation detector, in particular a scintillation detector according to any of the embodiments referred to above. The method comprises the following steps:

(a) forming first and second open channel layers, said first and second open channel layers each comprising a first/second bottom layer and first/second channel sidewalls, said first/second channel sidewalls defining a first/second set of adjacent channel portions arranged on top of said first/second bottom layer, (b) forming a separation layer (c) placing said separation layer on top of said first open channel layer such as to cover said first set of adjacent channel portions and bonding said separation layer to said first open channel layer, and (d) placing said second open channel layer upside down onto said separation layer such as to cover said second set of adjacent channel portions and bonding said separation layer to said second open channel layer, thereby integrally connecting said first and second open channel layers.

This way, the manufacturing scintillation detector can be easily and efficiently manufactured.

In a preferred embodiment, one or more of the first open channel layer, the second open channel layer and the separation layer are separately formed on top of a sacrificial material layer provided on a carrier substrate. The carrier substrate can then be released by removing the sacrificial material layer. This allows for separately manufacturing very thin and delicate layers which are each preliminarily supported and stabilized by the carrier substrate until the layers are integrally connected, as will be apparent from the preferred embodiment described below.

In a preferred embodiment, one or more of the bottom layer of the first and/or second open channel layers, the sidewalls of said first and/or second open channel layers or the separation layer are made from SU-8.

In a preferred embodiment, the method may further comprise a step of forming rib-like structures on the first/second bottom layers prior to forming said first/second channel sidewalls such as to lie within the adjacent channel portions when the first/second channel side walls are formed.

In addition, in step (a) and/or in step (b) a step of applying an optical coating to the first and second channel layers and/or to said separation layer may be included, wherein the optical coating can be one of a reflective metal coating or a coating having an index of refraction in the emission spectrum of the liquid scintillator to be used with said scintillation detector that is lower than that of the liquid scintillator, as mentioned before.

Finally, the method can be extended to manufacturing more than two layers. For this, one or more additional open channel layers can be manufactured in a way similar to the first and second open channel layers mentioned above. The additional open channel layer can then be placed upside down onto and bonded to the backside of the bottom layer of one of the first, second or another additional open channel layer. This way, an arbitrary number of layers can be manufactured and bonded together.

SHORT DESCRIPTION OF THE FIGURES

Figure 4A:
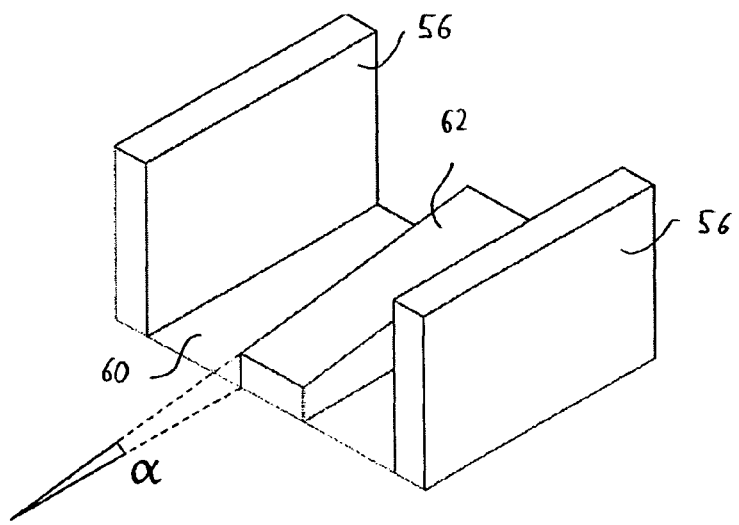
Figure 4B:
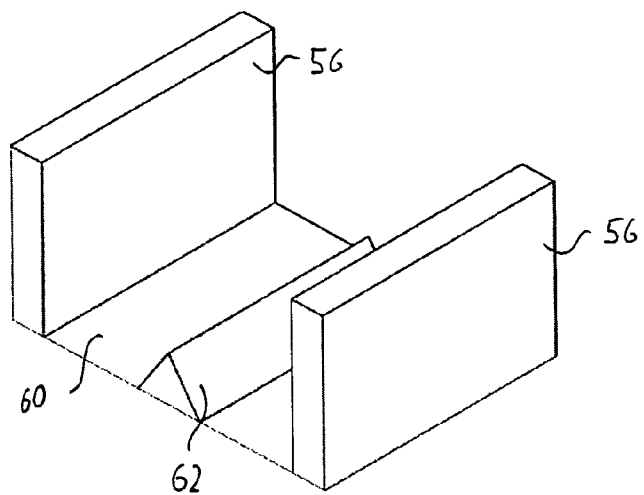
Figure 4C:
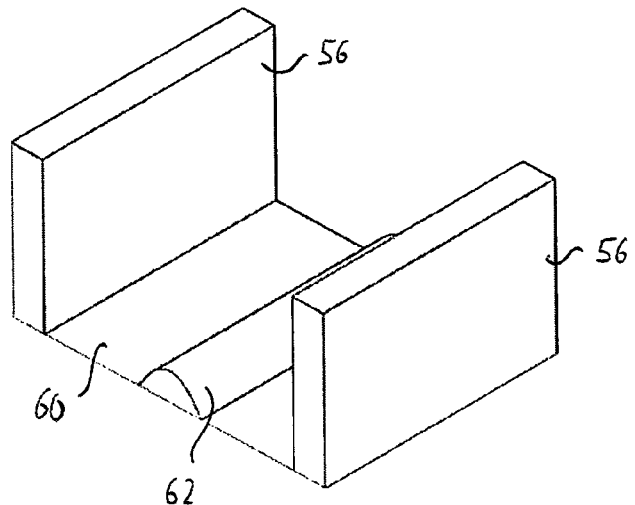

FIG. 4a-c are a perspective schematic views of channel portions including rib-like light guiding structures provided on their bottoms.

Figure 5:
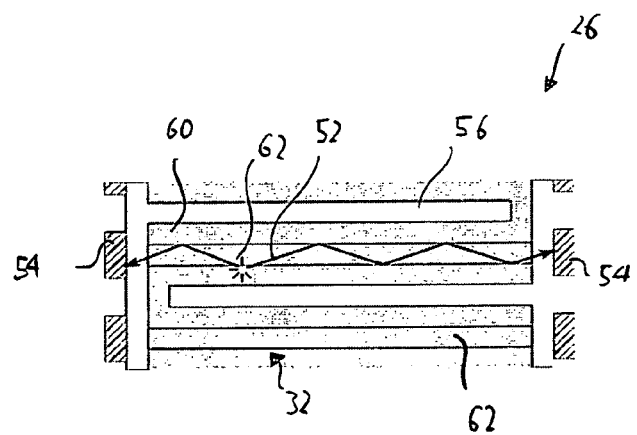

FIG. 5 is a plan view onto a portion of a channel structure employing the rib-like structure shown in FIGS. 4a to 4c and with photo detectors at each of the longitudinal ends of the rib-like structure.

Figure 6:
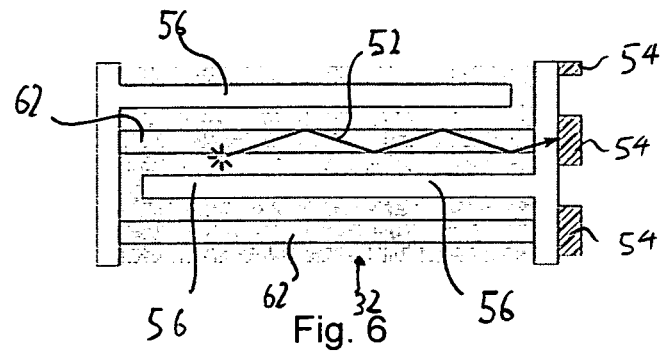

FIG. 6 is a plan view onto a portion of a channel structure employing the rib-like structure shown in FIGS. 4a to 4c and with a photo detector at one longitudinal end of the rib-like structure only.

Figure 7:
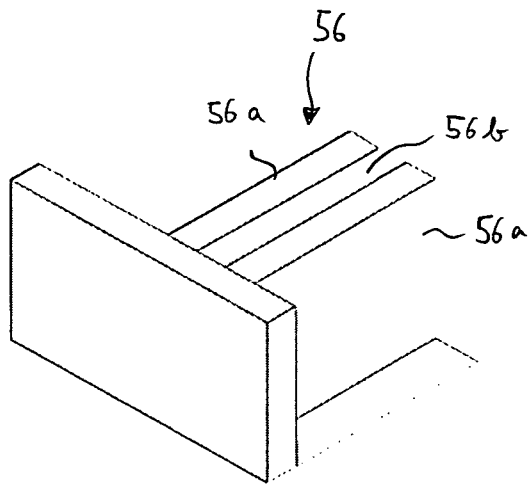

FIG. 7 is a perspective view of a portion of a channel structure with hollow sidewalls.

Figure 8:
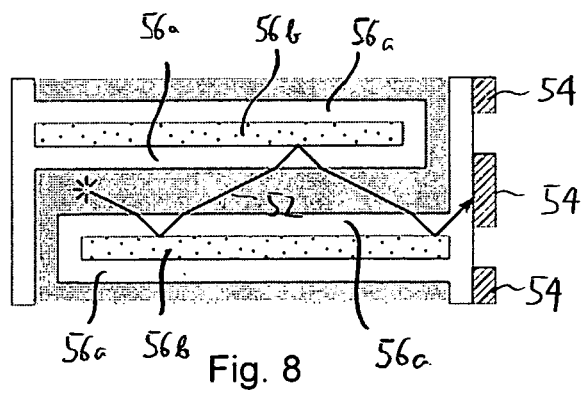

FIG. 8 is a schematic top plan view of a portion of a channel structure employing the hollow channel sidewall structure of FIG. 7.

Figure 9:
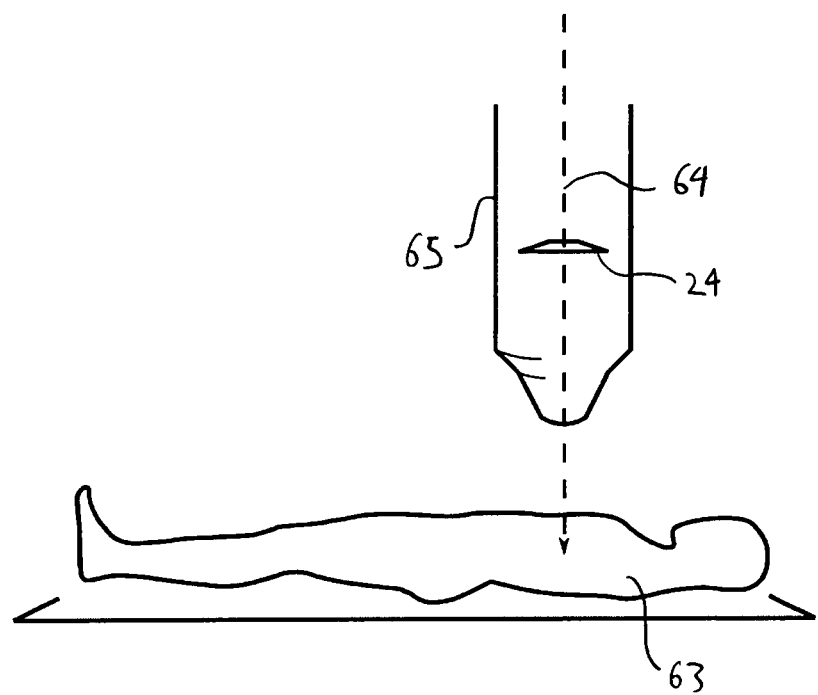

FIG. 9 is a schematic view illustrating the use of the detector for therapeutic beam profiling.

FIGS. 10a-h are schematic Figures illustrating manufacturing steps for manufacturing a scintillation detector according to the invention.

Figure 10:
Figure 10:
Figure 10:
Figure 10:
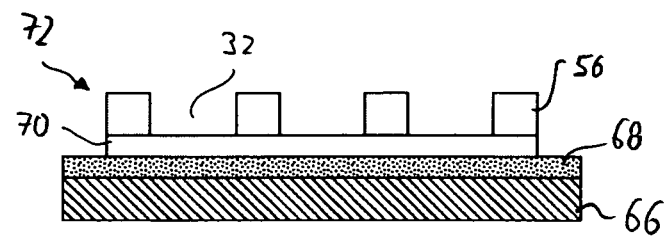
Figure 10:
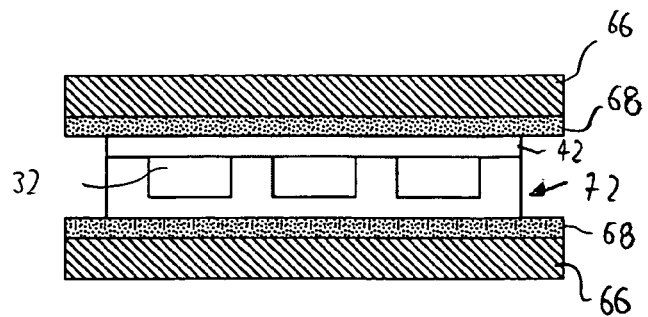
Figure 10:
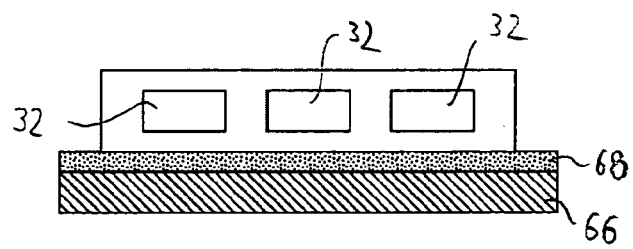
Figure 10:
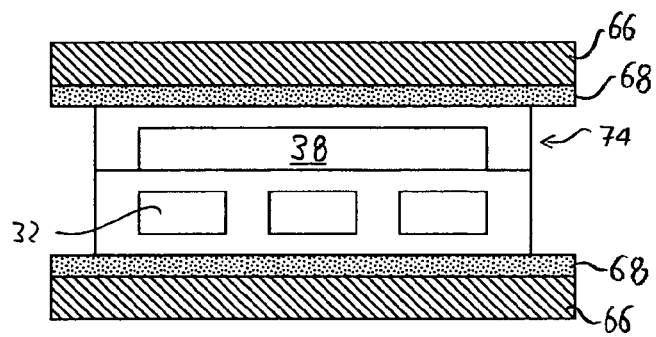
Figure 10:
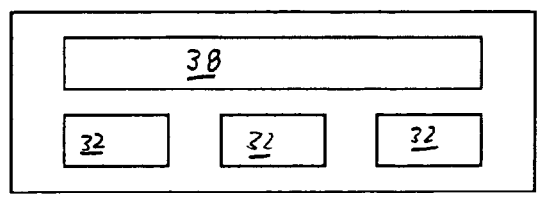

FIGS. 11a-d are schematic Figures illustrating alternative manufacturing steps to the manufacturing steps of FIG. 10.

DESCRIPTION OF THE PREFERRED EMBODIMENTS

For the purposes of promoting an understanding of the principles of the invention, reference will now be made to the preferred embodiments illustrated in the drawings and specific language will be used to describe the same. It will nevertheless be understood that no limitation of the scope of the invention is thereby intended, such alterations and further modifications in the illustrated device and method and such further applications of the principles of the invention as illustrated therein being contemplated therein as would normally occur now or in the future to one skilled in the art to which the invention relates.

Figure 2:
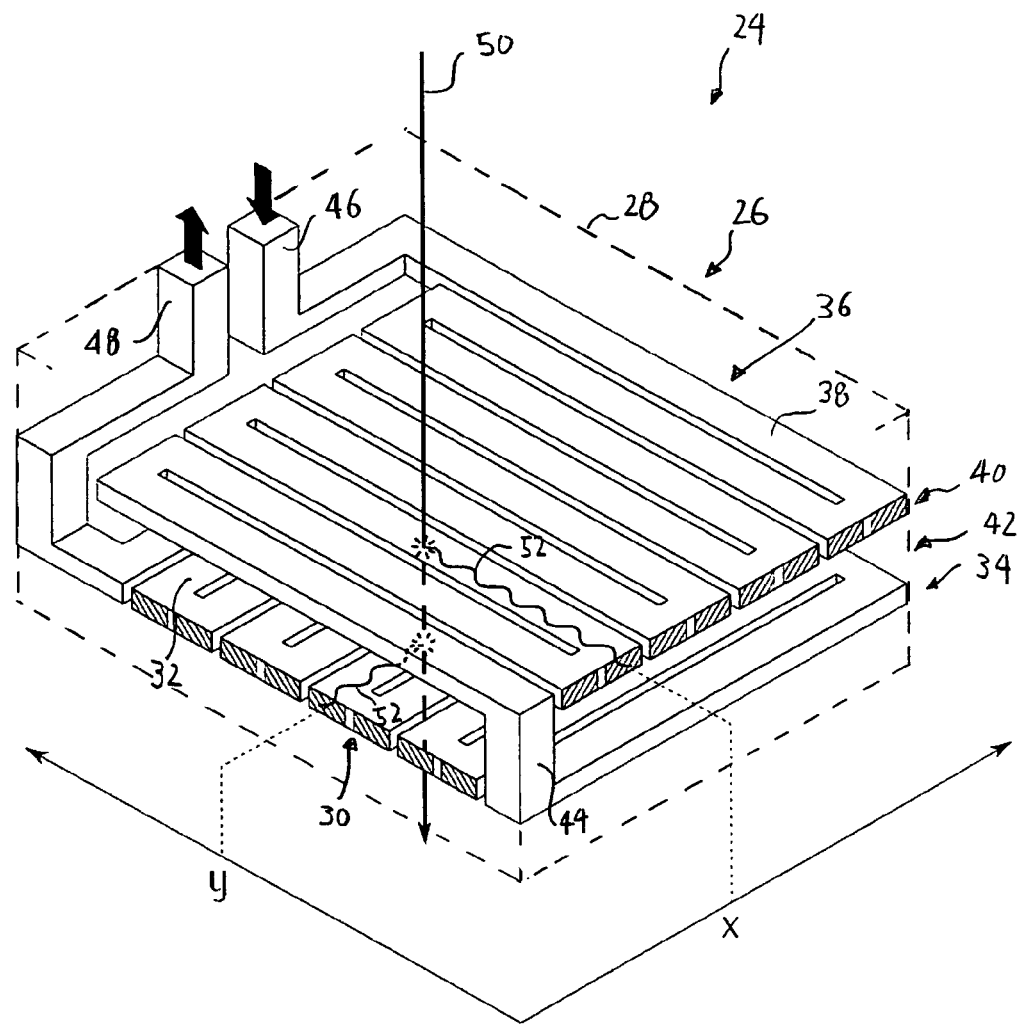
FIG. 2 is a schematic, perspective view of a microfabricated scintillation detector according to an embodiment of the invention, in which the bulk material has been omitted to better illustrate the channel structure.

FIG. 2 is a perspective view of a microfabricated scintillation detector 24. In FIG. 2, the bulk material of the scintillation detector has been omitted to provide a better view of the channel structure 26 employed by the scintillation detector 24. In other words, what is shown in FIG. 2 is basically the cavity of the channel structure 26 that is formed in the bulk material, where the bulk material is only indicated by the hatched line 28.

As is seen in FIG. 2, the channel structure 26 comprises a first set 30 of adjacent channel portions 32 arranged in a first layer 34. Further, the channel structure 26 comprises a second set 36 of adjacent channel portions 38 which are arranged in a second layer 40. The first and second layers 34, 40 are stacked on top of each other with a separation layer 42 in between. Since the bulk material is omitted in FIG. 2, the separation layer 42 only appears as an empty space. In reality, however, the separation layer 42 integrally connects the first and second layers 34 and 40.

In the embodiment shown in FIG. 2, the adjacent channel portions 32 of the first layer 34 are each parallel to each other, and the adjacent channel portions 38 of the second layer 40 are likewise parallel to each other. The channel portions 32, 38 of the first and second layers 34, 40 are arranged perpendicularly to each other.

As is seen in FIG. 2, the adjacent channel portions 32, 38 in each of the first and second layers 34, 40 are part of a corresponding serpentine-shaped channel in which neighboring channel portions 32, 38 are alternately connected at one of their longitudinal ends. However, in these serpentine-shaped channels, as mentioned before, the first and second sets of adjacent channel portions 30, 36 are directed at right angles with respect to each other. Also, due to the serpentine channel shape, all adjacent channel portions 32 of the first set 30 of channel portions are in fluid communication with each other, and all adjacent channel portions 38 of the second set 36 of channel portions are likewise in fluid communication with each other. Further, the two serpentine channels formed in the first and second layers 34, 40 are connected by a vertical channel portion 44, such that effectively all adjacent channel portions 32, 38 are part of a single, non-bifurcated channel running through the first and second layers 34, 40, with a single common inlet 46 and a single common outlet 48. In operation, the channel structure 26 is filled with a liquid scintillator material (not shown) that can be circulated through the channel structure 26 via the inlet 46 and the outlet 48.

According to the invention, the channel structure 26 simultaneously forms a light guiding structure for guiding scintillation light generated upon interaction of radiation with the liquid scintillator material in one of the adjacent channel portions 32, 38 towards a longitudinal end of the corresponding channel portion 32, 38. In particular, in FIG. 2, reference sign 50 resembles a particle trajectory which causes emission of scintillation light 52 upon interaction with the liquid scintillator in the channel structure 26. As is schematically shown in FIG. 2, in the illustrated embodiment the adjacent channel portions 32, 38 themselves serve as light guides guiding the scintillation light 52 towards the longitudinal end. At the end of each of the adjacent channel portions 32, 38, a photo detector 54 is provided for receiving the scintillation light 52. Since the adjacent channel portions 32, 38 in the first and second layers 34, 40 are arranged transversely to each other, the signals received at the associated photo detectors 54 allow to obtain two-dimensional information about the location of the scintillation event in an X-Y plane, where the X and Y coordinates correspond to the locations of the associated photo detectors 54, as illustrated in FIG. 2.

In order to confine the scintillation light 52 in the adjacent channel portions 32, 38, i.e. to make them act as light guides, the channel walls may be covered with a reflective coating, in particular a metal coating. A suitable metal coating would be a gold coating, but an even preferred material is an aluminum coating due to its better reflectivity in the emission spectrum of typical liquid scintillators.

In the alternative, at least part of the material that confines the adjacent channel portions 32, 38 and that is hence exposed to the liquid scintillator is a dielectric material having an index of refraction that is lower than that of the liquid scintillator for the relevant wave length, i.e. the wave length of the scintillation light that is to be guided. This way, the light is guided within the adjacent channel portions 32, 38 by means of total internal reflection, thereby avoiding a reflective metal coating. Avoiding a reflective metal coating has important advantages from a manufacturing point of view that will be explained in more detail below. However, avoiding the metal coating is also advantageous for minimizing the perturbation of the radiation field. Herein, the material that confines the adjacent channel portions could be the material of the channel walls themselves or a dielectric coating of the channel walls with a suitably low refractive index.

In order to allow for a total internal reflection, the refractive index of the portion of the channel walls in contact with the liquid scintillator should be 1.47 or below, more preferably 1.35 or below and most preferably 1.30 or below. Preferable materials to be used for the channel walls or for a coating applied to the channel walls are Pyrex glass, NOA 13685, NOA 1375, Perfluoroalkoxy or fluorinated (ethylenic-cyclooxyaliphatic substituted ethylenic) copolymer, but other low refractive index materials are likewise possible.

As was indicated in the introductory portion of the description, guiding the scintillation light by total internal reflection turns out to be surprisingly efficient and at least for longer light paths even more efficient than using a reflective metal coating. The reason, as mentioned before, is that although only a certain angular fraction of the scintillation light meets the condition of total internal reflection and will hence be guided along the channel portion, the attenuation of this fraction of the scintillation light that meets the total internal reflection condition will then be transported with comparatively moderate attenuation as compared to light that is multiply reflected from a metallic coating surface.

While it was generally stated that the channel structure simultaneously forms the light guiding structure, this does not necessarily imply that the adjacent channel portions 32, 38 themselves form the light guides, and it is neither necessary that the photo detectors 54 are precisely placed at the longitudinal ends of the adjacent channel portions 32, 38. Instead, alternative embodiments are possible, some of which being described with reference to FIGS. 3 to 8 below.

The scintillation detector 24 of FIG. 2 is made by microfabrication, i.e. making use of fabrication technologies generally known from semiconductor manufacturing, such as the deposition or growth of material on substrates or materials on top of each other, patterning, etching and the like. It turns out that by microfabrication the scintillation detector 24 can be manufactured efficiently and with great precision.

Further note that in the scintillation detector 24 of FIG. 2, the first and second layers 34, 40 are integrally connected via separation layer 42. This way, the first and second layers 34, 40 provide structural support for each other, which means that no or little further stabilizing material such as additional substrates are necessary. Also, it turns out that the separation layer 42 can in fact be made comparatively thin while still allowing for sufficient overall structural support of the scintillation detector 24. This way, the material budget of the scintillation detector 24 can be extremely low.

The thickness of the separation layer 42 separating the first and second layers 34, 40 is preferably 150 μm or less, more preferably 100 μm or less, even more preferably 60 μm or less and most preferably between 10 and 30 μm.

The height of the adjacent channel portions 32, 38 is preferably lower than 1000 μm, more preferably between 10 and 100 μm, which also corresponds to the thickness of the first and second layers 34, 40 as designated in FIG. 2. The width of the adjacent channel portions 32, 38 is preferably 500 μm or below, in particular 300 μm or below. In some embodiments, a suitable ratio of channel width:channel height of the adjacent channel portions is ≥0.5, preferably ≥1.0 and most preferably ≥1.5. Note in this regard that the schematic drawing of FIG. 2 is not meant to be on scale with regard to relative dimensions.

Note that the ratio of the width of and the pitch between adjacent channel portions 32, 38 in the corresponding layers 34, 40 defines a filling factor of the active detector portion which is smaller than one, since only the liquid scintillator within the channels actively participates in the radiation detection. In order to increase the filling factor to 100%, it is possible to provide further layers (not shown) such as a third and a fourth layer, each containing a third and a fourth set of adjacent channel portions, where the third (fourth) set of adjacent channel portions is arranged in parallel to, but staggered with regard to the channel portions in the first (second) set of adjacent channel portions.

Figure 3:
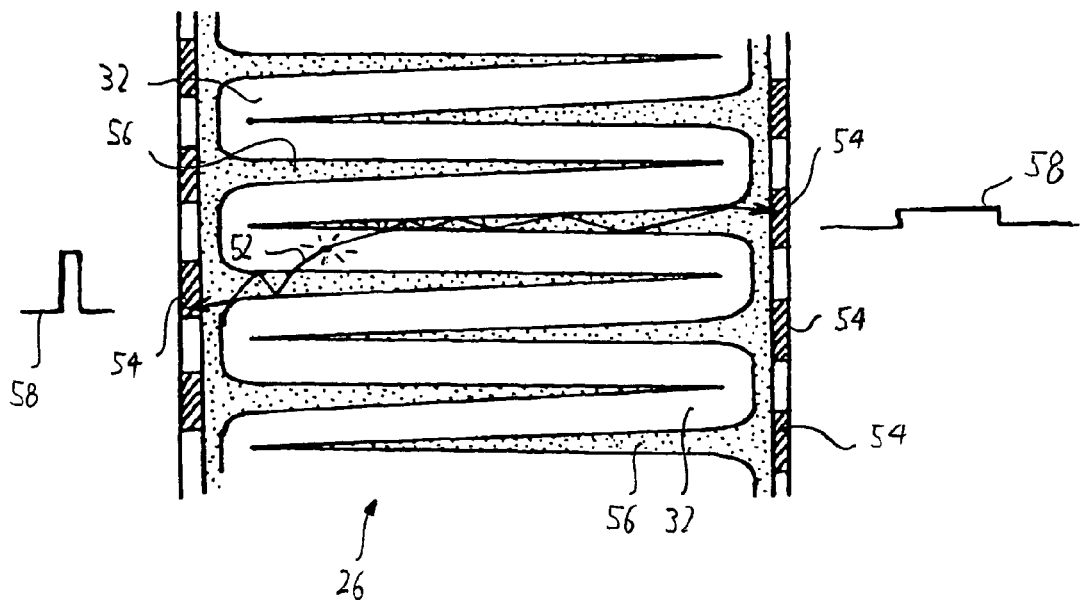
FIG. 3 is a schematic plan view onto a channel structure in which the sidewalls separating adjacent channel portions act as a light guide.

In FIG. 3, an alternative light guiding structure formed by a channel structure 26 is shown. FIG. 3 is a plan schematic view onto a serpentine-shaped channel comprising a plurality of parallel adjacent channel portions 32 which are separated by channel sidewalls 56. In the example of FIG. 3, the channel sidewalls 56 are not coated with a reflecting material or a low-refractive index material. Instead, it is assumed that the channel sidewalls 56 are made from a material having an index or refraction that is higher than that of the liquid scintillator (not shown) provided in the channel portion 32. Accordingly, the scintillation light 52 generated in the liquid scintillator will leave the corresponding channel portion 32 and enter the two channel sidewalls 56 adjacent to the channel portion 32, and will be guided therein towards the longitudinal ends of the channel portion 32, although not within the channel portions 32, but along the corresponding sidewall 56. Photo detectors 54 are provided such as to receive the scintillation light 52 guided along the channel sidewalls 56. In agreement with the interdigital structure of the channel sidewalls 56 employed for generating the serpentine channel geometry, the photo detectors 54 are alternately provided on opposite sides of the channel structure 26, as seen in FIG. 3. Note that in the embodiment of FIG. 3, the adjacent channel portions 32 are not parallel, but inclined with regard to each other, thereby leading to "triangular" or tapering thickness of the channel side walls 56 thereby effectively avoiding parallel opposing sidewall surfaces. This is to prevent that light that enters the channel side wall 56 at one surface will not leave the channel side wall at the opposite surface and enter the neighbouring channel. However, other channel side wall geometries allowing for light guiding are likewise possible.

As is further seen from FIG. 3, from one detector signal alone it cannot be decided in which of the two channel portions 32 adjacent to the corresponding channel sidewall 56 the scintillation light 52 was generated. However, since signals will be detected simultaneously at the photo detectors 54 associated with the two channel sidewalls 56 confining the channel portion 32 where the scintillation occurs, the origin of the scintillation light can be unambiguously attributed to one of the channel portions 32. For this, a suitable readout electronics (not shown) is provided that detects for such simultaneous events.

Further in FIG. 3, the signals 58 received at the left and right photo detectors 54 are schematically shown. Since the left photo detector 54 is farther away from the scintillation event than the right photo detector 54, the signal 58 at the left photo detector 54 will be more attenuated. However, since the location of the scintillation event along the length of the channel portion 32 is known from the other, perpendicular set of channel portions (not shown in FIG. 3), the attenuation can be compensated for numerically or the like. However, the relative attenuation between the left and right sensor signals 58 can also be used as an additional or independent way of determining the location of the scintillation event along the length of the corresponding channel portion 32, which essentially adds two-dimensional information to the signal.

Using the channel sidewalls 56 as the light guides is a very elegant and simple way to guide the scintillation light towards the longitudinal end of the corresponding channel portion 32, 38. However, this embodiment may have to cope with some degree of cross-talk, since the channel sidewalls 56 will typically be optically connected via the bottom and top walls (not shown) of the channel.

An alternative embodiment making use of the same principle of light guiding is shown in FIGS. 4a to 4c. In each of FIGS. 4a to 4c, again a channel portion 32 is schematically shown which is confined by two channel sidewalls 56 and a bottom surface 60. On top of the bottom surface 60, a rib-like structure 62 is provided which has an index of refraction that is higher than that of the liquid scintillator (not shown) to be used in the detector, where the rib-like structure 62 forms part of the "channel confining material" that is exposed to the liquid scintillator in operation. Due to its higher index of refraction, the rib-like structure 62 will capture scintillation light and guide the same to a corresponding photo detector (not shown in FIG. 4) in much the same way as is the case for the sidewall 56 in FIG. 3, but with reduced cross-talk. Note that using microfabrication technologies, such rib-like structures 62 can be readily formed on top of the bottom surface 60.

Again, the geometries of the rib-like structures 62 are in each case chosen such as to avoid that light captured thereby immediately exits the rib-like structure, basically by avoiding parallel exit and entrance surfaces. For this purpose, FIG. 4a shows a ramp-like structure, 4b shows a structure with a triangular cross section and FIG. 4c a structure with a semi-circular cross section. Note that the configurations of FIGS. 4b, 4c can be combined with that of FIG. 4a, i.e. it would be possible to provide rib-like structures 62 having a varying height and a triangular or semi-circular cross section. Also, an optical coating may be provided between the bottom surface 60 and the rib-like structure 62. rib-like structures 62 as shown in FIGS. 4a to 4c can be obtained, for example, out of SU-8 by the so-called grey-tone photolithography technique.

FIGS. 5 and 6 show again schematic plan views of a portion of a channel structure 26 employing the rib-like structure 62 provided on the bottom surface 60 of the channel portion 32. In the embodiment of FIG. 5 two photo detectors 54 are associated with each rib-like structure 62, one provided at each end thereof. Herein, the idea is that the location of the scintillation event within the channel portion 32 can be determined by comparing the attenuation of the two signals received. FIG. 6 is an alternative embodiment with only one photo detector 54 associated with each rib-like structure 62.

A yet further embodiment is shown in FIGS. 7 and 8. In FIG. 7, the channel sidewall 56 has a layered or hollow structure, with two material layers 56a and an air-filled or vacuum gap 56b in between. The wall part 56a may be of a material having an index of refraction that is higher than that of the liquid scintillator. However, the reflective index of the gap 56b corresponds to that of air or vacuum, i.e. n=1. Accordingly, for a large range of angles of incidence, light will be reflected at the interface between material layer 56a and gap 56b as indicated in FIG. 8. So effectively, the layered or hollow wall structure of FIG. 7 behaves similarly to a sidewall with a very low index of reflection, while still taking advantage of the liberty to use high reflective index materials for manufacturing the wall parts 56a.

The scintillation detector 24 according to one of the various embodiments should find practical use in many fields where a low material budget and considerable radiation hardness are necessary. Note that the radiation hardness is intrinsically achieved by the fact that the scintillator material can be exchanged as needed, or can even be continuously exchanged by providing a continuous flow of scintillator liquid through the channel structure 26. Also, the detector design allows for exchanging the liquid scintillator depending on the application or type of radiation to be detected, thereby making the scintillation detector 24 of the invention highly universal.

Figure 1:
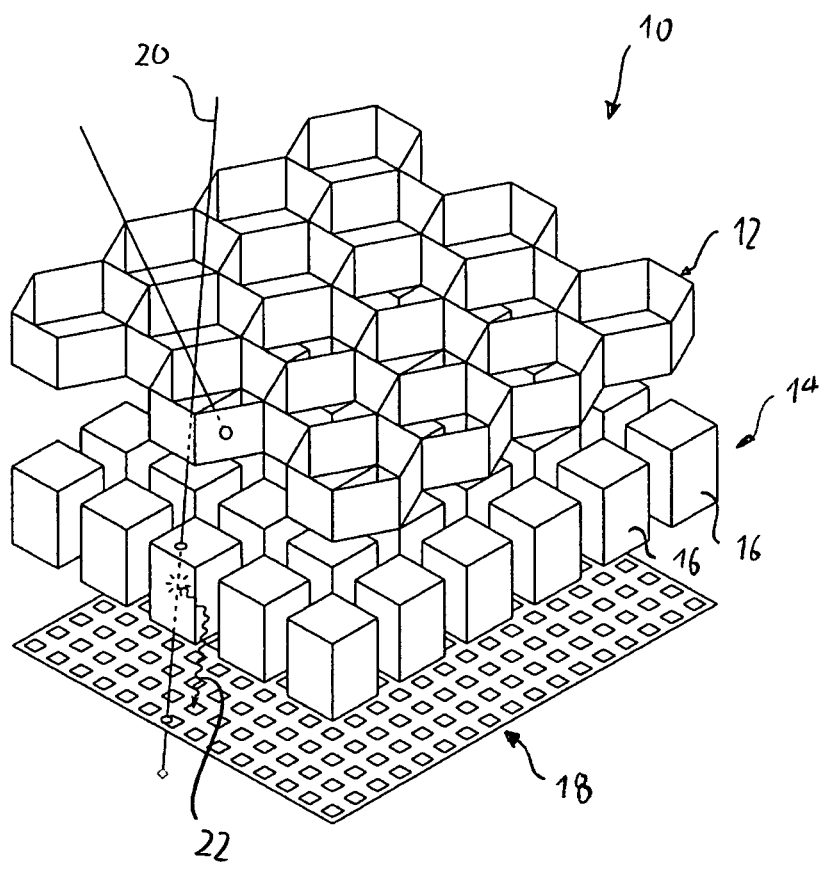
FIG. 1 is a perspective exploded view of a prior art scintillation detector.

A very attractive use of the scintillation detector 24 of the invention is in the field of beam monitoring in hadron therapy, as is schematically shown in FIG. 9. In FIG. 9 a patient 63 undergoing hadron therapy using a particle beam 64 provided from a beam pipe 65 is schematically shown. Within the particle beam 64, a scintillation detector 24 according to an embodiment of the present invention is provided, which allows to determine the radiation profile of the beam 64. Since the liquid scintillator can be exchanged at any time, the sensitive part of the detector will not be prone to "aging" in spite of the considerable dose provided by the particle beam 64. Further, since the photo detectors 54 are provided at the side of the detector plane (see FIG. 2), rather than within the detector plane, as is the case in the prior art scintillation detector of FIG. 1, the photo detectors 54 can be kept outside the particle beam 64 and will not be damaged thereby. A further advantage of this structure is that the number of photo detectors 54 scales linearly with the detector diameter, rather than quadratically, as would be the case in the ordinary design of FIG. 1.

Further, for the reasons explained above, the scintillation detector 24 has a very low material budget which means that it has only little effect on the particle beam 64 passing therethrough. This will allow to constantly keep the scintillation detector 24 in the particle beam during operation, which means that the particle beam can be monitored in real-time during therapy. To the knowledge of the applicant, this is different from any known beam profiler currently used in hadron beam therapy, which are only inserted into the beam path for calibration but removed from the beam path during application of the beam to the patient. From an operational point of view, it is however highly advantageous to monitor the beam in real-time during treatment, such as to become aware of any errors in the beam profile and such as to constantly monitor the dose.

FIG. 10(a)-(h) are a sequence of Figures illustrating the manufacturing steps according to a method of manufacturing a scintillation detector 24 according to the present invention. The method starts with providing a substrate 66 such as a silicon substrate (FIG. 10(a)). In the next step, a sacrificial material film 68, e.g. a PET film, is deposited onto the substrate 66 (FIG. 10(b)). Next, a thin layer 70 of structural material is formed on top of the sacrificial material layer 68 (FIG. 10(c)). A suitable structural material is for example SU-8. The layer 70 eventually forms the bottom walls of the channel portions 32. Thereafter, a second layer of structural material is provided and patterned such as to form the sidewalls 56 of the channel structure 26 (FIG. 10(d)). The structural material may be the same as that of layer 70. Also in this step, an optical coating may be provided covering the sidewalls 56 and the channel bottom provided by layer 70. Herein, an optical coating can again be a metal coating, such as aluminum or gold, or a coating having a low index of refraction such as to allow light guiding image channel portions 32 by a total internal reflection. The structure shown in FIG. 10(d) corresponds to the "first open channel layer" 72 that was referred to in the introductory portion.

Next, a separation layer 42 is provided on a substrate 66, on top of a sacrificial material film 68, in a similar way as described in FIGS. 10(a) to 10(c). The separation layer 42 is placed on top of the first open channel layer 72 such as to cover the first set of adjacent channel portions 32, and the separation layer 42 is bonded to said first open channel layer 72 (see FIG. 10(e)). The lower surface of the separation layer 42 facing the first set of channels 32 may also be optically coated, if desired.

In the next step, the substrate 66 is removed from the separation layer 42 by removing the sacrificial material layer 68 to yield a structure as shown in FIG. 10(f).

Next, a second open channel layer 74 is manufactured generally in the same way as described with reference to FIGS. 10(a) to 10(d) for the first open channel layer 72. Then, the second open channel layer 74 is placed upside down onto the separation layer 42 such as to cover the second set of adjacent channel portions 38, as shown in FIG. 10(g). Note that in FIG. 10(g), the second channel portion 38 extends along the paper plane, while the first channel portions 32 extend perpendicularly to the paper planes.

Finally, the top and bottom substrates 66 can be released by removing all of the sacrificial material 68, thereby obtaining an integrated monolithic structure with two channel layers embedded.

While in FIG. 10 only the formation of two channel layers has been shown, the manufacturing method can be easily extended to higher numbers of channel layers. For this, additional open channel layers would be manufactured in a similar way as shown in FIGS. 10a to 10d and could then be attached to the backside of the bottom layers 70 of one of the first or second open channel layers 72, 74, i.e. attached to the top or the bottom of the configuration shown in FIG. 10h.

Further, the general manufacturing method summarized in FIG. 10 can be modified such as to include rib-like structures 62 as discussed with reference to FIGS. 4a to 4c. FIGS. 11a to 11d are a sequence of figures illustrating only manufacturing steps deviating from the manufacturing steps shown in FIGS. 10c to 10h such as to highlight the difference.

Figure 11A:
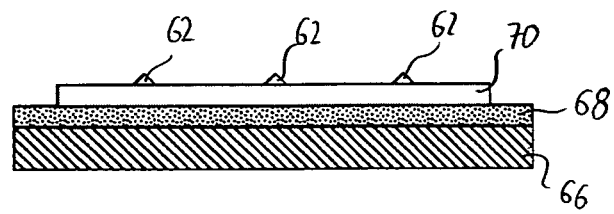
Figure 11B:
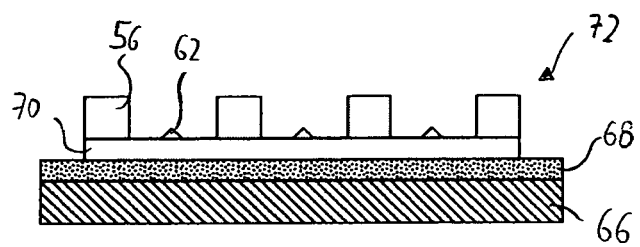
Figure 11C:
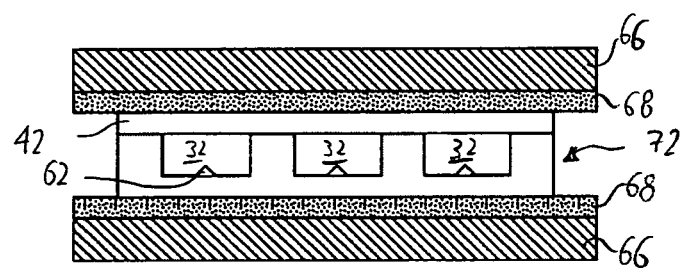
Figure 11D:
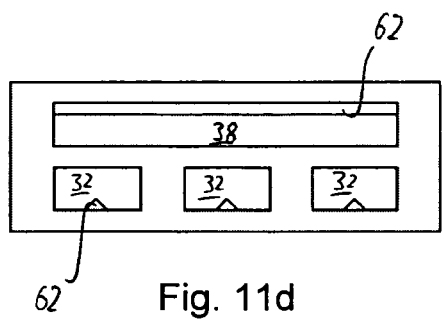

In particular, FIG. 11a shows a step that would follow after the step of FIG. 10c, and in which rib-like structures 62 are formed on the bottom layer 70, which in the present example are rib-like structures 62 with triangular cross sections similar to those of FIG. 4b. In FIGS. 11b and 11c the channel sidewalls 56 are formed and the separation layer 42 is placed on top of the channel sidewall 56 such as to cover the first set of adjacent channel portions 32. FIG. 11d shows the final integrated structure corresponding to that shown in FIG. 10h but with rib-like structures 62 provided at the channel bottoms.

The embodiments described above and the accompanying figures merely serve to illustrate the scintillation detector and its manufacturing method according to the present invention, and should not be taken to indicate any limitation of the detector and manufacturing method. The scope of the patent is solely determined by the following claims.

LIST OF REFERENCE SIGNS 10 prior art scintillator detector
12 collimator grid
14 scintillating material layer
16 pillars of scintillating material
18 photo detector matrix
20 particle trajectory
22 scintillation flash
24 scintillation detector of the invention
26 channel structure
28 broken line indicating bulk material
30 first set of adjacent channel portions
32 channel portion
34 first layer
36 second set of adjacent channel portions
38 channel portion
40 second layer
42 separation layer
44 vertical channel portion
46 inlet
48 outlet
50 particle trajectory
52 scintillation light
54 photo detector
56 channel sidewall
56a outer portion of channel side wall 56
56b hollow portion of channel sidewall 56
58 signal of photo detector 54
60 bottom surface of channel portion 32
62 rib-like structure
63 patient
64 particle beam
65 beam pipe
66 substrate
68 sacrificial material layer
70 structural material layer
72 first open channel layer
74 second open channel layer

The invention claimed is:

1. A microfabricated scintillation detector, comprising
a channel structure for containing a liquid scintillator material therein and flowing said liquid scintillator material therethrough,
said channel structure comprising a first set of adjacent channel portions arranged in a first layer and in fluid communication with each other, and
a second set of adjacent channel portions arranged in a second layer and in fluid communication with each other, said second set of adjacent channel portions being directed transversely with respect to the first set of adjacent channel portions,
wherein said first and second layers are stacked on top of each other with a separation layer in between, said separation layer integrally connecting said first and second layers,
wherein the channel structure simultaneously forms a light guiding structure for guiding scintillation light generated upon interaction of radiation with said liquid scintillator material in said adjacent channel portions towards a longitudinal end of the corresponding channel portion,
said scintillation detector further comprising a plurality of photo detectors, arranged to receive said scintillation light.

2. The microfabricated scintillation detector of claim 1, wherein the channel portions in the first set of adjacent channel portions are arranged in parallel to each other in said first layer, and/or the channel portions in the second set of adjacent channel portions are arranged in parallel to each other in said second layer,
wherein said second set of adjacent channel portions is directed at right angles with respect to the first set of adjacent channel portions.

3. The microfabricated scintillation detector of claim 1, wherein the plurality of photo detectors are arranged in proximity to the longitudinal ends of the adjacent channel portions,
or coupled with locations in proximity to the longitudinal ends of the adjacent channel portions by optical fibers.

4. The microfabricated scintillation detector of claim 1, wherein said first and second sets of adjacent channel portions are in fluid communication with each other.

5. The microfabricated scintillation detector of claim 1, wherein each of said first and second sets of adjacent channel portions are part of a corresponding serpentine shaped channel, in which neighboring portions are alternately connected at one of their longitudinal ends.

6. The microfabricated scintillation detector of claim 5, wherein the serpentine channels formed in the first and second layers are connected by a vertical channel portion passing said separation layer such as to form a single channel running through said first and second layers.

7. The microfabricated scintillation detector of claim 1, wherein the thickness of the separation layer separating the adjacent channel portions in said first and second layers is 150 μm or less.

8. The microfabricated scintillation detector of claim 1, wherein the width of said adjacent channel portions is 500 μm or below.

9. The microfabricated scintillation detector of claim 1, wherein the height of the adjacent channel portions is 1000 μm or below.

10. The microfabricated scintillation detector of claim 1, wherein the ratio of channel width to channel height of the adjacent channel portions is >0.5.

11. The microfabricated scintillation detector of claim 1, wherein the plurality of photo detectors is formed by an array of photo detectors having the same pitch as the corresponding channel portions in said first and second sets of adjacent channel portions.

12. The microfabricated scintillation detector of claim 1, further comprising a third and/or a fourth set of adjacent channel portions arranged in a third and fourth layer, respectively,
wherein the channel portions in said third/fourth set of adjacent channel portions are arranged in parallel to and staggered with regard to the channel portions in said first/second set of adjacent channel portions.

13. The microfabricated scintillation detector of claim 1, wherein the channel walls defining said adjacent channel portions are made from or covered with a dielectric material having a refractive index in the emission spectrum of a liquid scintillator to be used in said scintillation detector that is lower than that of the liquid scintillator,
in particular a refractive index of 1.47 or below,
and wherein the dielectric material is Pyrex glass, NOA 13685, NOA 1375, Perfluoroalkoxy and/or fluorinated (ethylenic-cyclo oxyaliphatic substituted ethylenic) copolymer.

14. The microfabricated scintillation detector according to claim 1, wherein the channel walls are covered with a reflective coating.

15. The microfabricated scintillation detector according to claim 1, wherein at least a part of the channel confining material exposed to the liquid scintillator when in operation has an index of refraction that is higher than that of the liquid scintillator to be used in said microfabricated scintillation detector, said higher refractive index material acting as a light guide for capturing scintillation light and guiding the same to a corresponding photo detector.

16. The microfabricated scintillation detector of claim 13, wherein said channel con-fining material acting as a light guide is formed by the side walls separating neighboring channel portions,
   wherein the photo detectors are associated with respective ones of said sidewalls such as to receive scintillation light guided through the respective sidewall, and
   wherein the scintillation detector further comprises a readout means for detecting simultaneous signals corresponding to adjacent sidewalls confining the same channel portion.

17. The microfabricated scintillation detector of claim 13, wherein said channel confining material acting as a light guide is formed by a rib-like structure provided on the bottom of said adjacent channel portions.

18. The microfabricated scintillation detector according to claim 1, wherein the channel sidewalls have outer portions that are exposed to the scintillator liquid when in operation and that have an index of refraction that is similar to or higher than that of the scintillator liquid to be used with said detector, and an inner portion having an index of refraction that is lower than that of the scintillator liquid.

19. A beam profiler for monitoring the radiation profile of a medical radiation beam, said beam profiler comprising: a microfabricated scintillation detector according to claim 1, and a readout means for receiving signals from the photo detectors and calculating beam profile information therefrom.

20. A radiation therapy apparatus, said apparatus being configured to monitor the medical radiation beam, during therapy using a beam profiler according to claim 19.

21. A method of manufacturing a scintillation detector, said method comprising:
   (a) forming first and second open channel layers, said first and second open channel layers each comprising a first/second bottom layer and first/second channel sidewalls, said first/second channel sidewalls defining a first/second set of adjacent channel portions adjacently arranged on top of said first/second bottom layer;
   (b) forming a separation layer;
   (c) placing said separation layer on top of said first open channel layer such as to cover said first set of adjacent channel portions and bonding said separation layer to said first open channel layer;
   (d) placing said second open channel layer upside down onto said separation layer such as to cover said second set of adjacent channel portions and bonding said separation layer to said second open channel layer, thereby integrally connecting said first and second open channel layers.

22. The method of claim 21, wherein one or more of
   the first open channel layer,
   the second open channel layer, and
   the separation layer
   are separately formed on top of a sacrificial material layer provided on a carrier substrate, and wherein the carrier substrate is released by removing the sacrificial material layer.

23. The method of claim 21, wherein one or more of
   the bottom layer of said first and/or second open channel layers,
   the sidewalls of said first and/or second open channel layers, or
   the separation layer
   are made from SU-8.

24. The method of claim 21, further comprising forming rib-like structures on the first/second bottom layers prior to forming said first/second channel sidewalls such as to lie within the adjacent channel portions when the first/second channel sidewalls are formed.

25. The method of claim 19, wherein (a) and/or (b) comprises applying an optical coating to said first and second channel layers and/or said separation layer,
   said optical coating comprising one or more of
      a reflective metal coating, in particular and aluminum or gold coating, or
      a dielectric coating having an index of refraction in the emission spectrum of the liquid scintillator to be used with said scintillation detector that is lower than that of said liquid scintillator,
   wherein the refractive index is 1.47 or below,
   wherein the dielectric coating is one or more of Pyrex glass, NOA 13685, NOA 1375, Perfluoroalkoxy and/or fluorinated (ethylenic-cyclo oxyaliphatic substituted ethylenic) co-polymer.

26. The method according to claim 21, further comprising forming one or more additional open channel layers, each additional open channel layer comprising a bottom layer and channel side walls defining a set of adjacent channel portions on top of said bottom layer,
   and placing said additional open channel layer upside down onto and bonding it to the backside of the bottom layer of one of the first, the second or another additional open channel layer.

* * * * *